US011193143B2

(12) United States Patent
Ross et al.

(10) Patent No.: US 11,193,143 B2
(45) Date of Patent: Dec. 7, 2021

(54) GRAIN PROCESSING

(71) Applicant: Blaygow Limited, St. Helier (GB)

(72) Inventors: John Morris Ross, Girvan (GB); Cornelius Martin Lynch, Girvan (GB)

(73) Assignee: Blaygow Limited, St. Helier (GB)

( * ) Notice: Subject to any disclaimer, the term of this patent is extended or adjusted under 35 U.S.C. 154(b) by 224 days.

(21) Appl. No.: 16/023,625

(22) Filed: Jun. 29, 2018

(65) Prior Publication Data
US 2019/0002928 A1 Jan. 3, 2019

Related U.S. Application Data

(63) Continuation of application No. 14/443,362, filed as application No. PCT/GB2013/053010 on Nov. 15, 2013, now abandoned.

(30) Foreign Application Priority Data

Nov. 16, 2012 (GB) ........................... 1220599
Nov. 16, 2012 (GB) ........................... 1220608

(51) Int. Cl.
*C12P 5/02* (2006.01)
*C02F 3/28* (2006.01)
C02F 103/32 (2006.01)

(52) U.S. Cl.
CPC .............. *C12P 5/023* (2013.01); *C02F 3/28* (2013.01); *C02F 2103/32* (2013.01); *C02F 2209/06* (2013.01); *Y02E 50/30* (2013.01)

(58) Field of Classification Search
CPC ............. C12P 5/023; C02F 3/28; C02F 3/286
See application file for complete search history.

(56) References Cited

U.S. PATENT DOCUMENTS

| 441,543 | A | 11/1890 | Enholm |
| 4,067,801 | A | 1/1978 | Ishida et al. |
| 4,352,738 | A | 10/1982 | Blay et al. |
| 4,429,043 | A | 1/1984 | Paton |
| 5,228,995 | A | 7/1993 | Stover |
| 2002/0079266 | A1 | 6/2002 | Ainsworth et al. |
| 2005/0194311 | A1 | 9/2005 | Rozich |
| 2007/0141691 | A1 | 7/2007 | Hirl |
| 2008/0213429 | A1 | 9/2008 | Binder et al. |
| 2009/0023193 | A1 | 1/2009 | Murphy et al. |
| 2009/0239279 | A1 | 11/2009 | Hall et al. |
| 2009/0280557 | A1 | 11/2009 | Ejlertsson |
| 2010/0018917 | A1 | 1/2010 | Fitch et al. |
| 2010/0196979 | A1 | 8/2010 | Birkmire et al. |
| 2010/0221804 | A1 | 9/2010 | Veit Eberhard et al. |
| 2011/0020862 | A1 | 1/2011 | Audebert et al. |
| 2012/0021500 | A1 | 1/2012 | Ejlertsson et al. |
| 2014/0356927 | A1 | 12/2014 | Ross et al. |

FOREIGN PATENT DOCUMENTS

| CN | 2143226 | Y | 10/1993 |
| CN | 101157937 | A | 4/2008 |
| CN | 101195504 | A | 6/2008 |
| CN | 101265002 | A | 9/2008 |
| CN | 101319230 | A | 12/2008 |
| CN | 101565719 | A | 10/2009 |
| CN | 101805753 | A | 8/2010 |
| CN | 101899473 | A | 12/2010 |
| DE | 4000834 | A1 | 8/1990 |
| DE | 19717965 | A1 | 10/1998 |
| DE | 19937876 | A1 | 3/2001 |
| DE | 10316680 | A1 | 11/2004 |
| DE | 102008015609 | A1 | 10/2009 |
| DE | 202009014905 | U1 | 5/2010 |
| DE | 102009009985 | A1 | 8/2010 |
| EP | 0152730 | A1 | 8/1985 |
| EP | 0414539 | A1 | 2/1991 |
| EP | 1259466 | A1 | 11/2002 |
| EP | 1792877 | A1 | 6/2007 |
| EP | 1997901 | A2 | 12/2008 |
| EP | 2135938 | A1 | 12/2009 |
| EP | 2226295 | A2 | 9/2010 |
| EP | 2268787 | A2 | 1/2011 |
| EP | 2398743 | A1 | 12/2011 |
| EP | 2419516 | A1 | 2/2012 |
| JP | 02063599 | | 3/1990 |
| JP | H047498 | A | 1/1992 |
| JP | 2004025088 | A | 1/2004 |
| JP | 2004243259 | A | 9/2004 |

(Continued)

OTHER PUBLICATIONS

WtERT ("Anerobic Digestion Process", Waste-to-Energy Reserach and Technology Council, Emmanuel Serna, 2009, available at www.wtert.eu/default.asp?Menue=13&ShowDok=12) (Year: 2009).*
Japanese Office Action, filed in JP application No. 2015-542354, dated Dec. 12, 2019, pp. 1-5.
European Exam Report for correspondence EP Application 13798376.3 dated Nov. 8, 2018, pp. 1-7.
Buivid MG, & Wise DL, "Fuel gas enhancement by controlled landfilling of municipal solid waste", Resources and Conservation, vol. 6, pp. 3-20 (1981).
Moletta R, "Winery and distillery wastewater treatment by anaerobic digestions", Water Science & Technology, vol. 51, pp. 137-144 (2005).

(Continued)

Primary Examiner — Robert J Yamasaki
Assistant Examiner — Charles Zoltan Constantine
(74) Attorney, Agent, or Firm — Wolter Van Dyke Davis, PLLC; Eugene T. Molinelli; Martha Cassidy

(57) ABSTRACT

The present invention provides a process for producing biogas and/or methane from solid spent cereal products derived from, for example, the mashing process of malt whisk(e)y and/or beer production. There is also provided a system for producing biogas and/or methane from solid spent cereal products derived from, for example, the mashing process of malt whisk(e)y and/or beer production.

20 Claims, 5 Drawing Sheets

(56) References Cited

FOREIGN PATENT DOCUMENTS

| | | |
|---|---|---|
| JP | 2004298677 | 10/2004 |
| JP | 2006312120 A | 11/2006 |
| JP | 2007216207 A | 8/2007 |
| JP | 2009219960 A | 10/2009 |
| JP | 2009248041 A | 10/2009 |
| KR | 20070034556 | 10/2008 |
| KR | 20090028147 | 10/2010 |
| SE | 464520 B | 5/1991 |
| WO | 2006124781 A2 | 11/2006 |
| WO | 2008108599 A1 | 9/2008 |
| WO | 2009090476 A8 | 7/2009 |
| WO | 2009102142 A2 | 8/2009 |
| WO | 2009103866 A2 | 8/2009 |
| WO | 2010124147 A1 | 10/2010 |
| WO | 2010147928 A1 | 12/2010 |
| WO | 2011015328 A1 | 2/2011 |
| WO | 2011/066866 | 6/2011 |
| WO | 2011122056 A1 | 10/2011 |
| WO | 2011143667 A2 | 11/2011 |
| WO | 2012/001417 | 1/2012 |
| WO | 2013/104911 | 7/2013 |
| WO | 2014/076483 | 5/2014 |

OTHER PUBLICATIONS

Neira K, et al., "Anaerobic co-digestion of surplus yeast and wastewater to increase energy recovery in breweries", Water Science & Technology, vol. 61, Issue 5, p. 1129 (2010).
Parawira W, et al., "A study of two-stage anaerobic digestion of solid potato waste using reactors under mesophilic and thermophilic conditions", Environmental Technology, vol. 28, pp. 1205-1216 (2007).
Sezun M, et al., "Anaerobic digestion of brewery spent grain in a semi-continuous bioreactor: inhibition by phenolic degradation products", ACTA Chimica Slovenica, vol. 58, pp. 158-166 (2011).
Zupancic GD, et al., "Anaerobic co-digestion of excess brewery yeast in a granular biomass reactor to enhance the production of biomethane", Bioresource Technology, vol. 124, pp. 328-337 (2012).
Li, P., et al., "Anaeroic Treatment of Waste Beer", "Environmental Progress", Apr. 2005, pp. 88-95, vol. 24, No. 1, Publisher: Wiley, Published in: DOI 10.1002/ep.10041.
Loewenthal, R., et al., "Modelling Struvite Precipitation in Anaerobic Treatment Systems", "Water Science Technology", Dec. 1994, pp. 107-116, vol. 30, No. 12, Publisher: IWA Publishing, Published in: https://search-proquest-com.mutex.gmu.edu/docview/1943311856?accountid=14541.
Melamane, X., et al., "Anaerobic digestion of fungally pre-treated wine distillery wastewater", "African Journal of Biotechnology", Dec. 5, 2007, pp. 1990-1993, vol. 6, No. 17, Publisher: Academic Journals, Published in: http://www.academicjournals.org/AJB.
Melchior, J., et al., "Biomethanation: Its future development and the influence of the physiology of methanogenesis", "Journal of Chemical Technology and Biotechnology", 1/11982, pp. 189-197, vol. 32, Publisher: John Wiley & Sons, Ltd, Published in: https://doi.org/10.1002/jctb.5030320123.
Murray, W., et al., "Effects of Nickel, Cobalt, and Molybdenum on Performance of Methanogenic Fixed-Film Reactors", "Applied and Environmental Microbiology", Sep. 1981, pp. 502-505, vol. 42, No. 3, Published in: https://www.ncbi.nlm.nih.gov/pmc/articles/PMC244044/.
Pecharaply, Athapol, et al., "Influence of Anaerobic Co-Digestion of Sewage and Brewery Sludges on Biogas Production and Sludge Quality", "Journal of Environmental Science and Health Pt. A", 2007, pp. 911-923, vol. 42, Publisher: Taylor & Francis, Published in: DOI: 10.1080/10934520701369818.
Saritpongteeraka, K., et al, "Effects of pH adjustment by parawood ash and effluent recycle ratio on the performance of anaerobic baffled reactors treating high sulfate wastewater", "Bioresource Technology", Dec. 2008, pp. 897-8994, vol. 99, No. 18, Publisher: Elsevier, Published in: doi:10.1016/j.biortech.2008.05.012.
Shao, X., et al., "Treatment of brewery wastewater using anaerobic sequencing batch reactor (ASBR)", "Bioresource Technology", May 2008, pp. 3182-3186, vol. 99, No. 8, Publisher: Elsevier Ltd., Published in: doi:10.1016/j.biortech.2007.05.050.
Tokuda, Masatsugu, et al., "Methane Fermentation of Pot Ale from a Whisky Distillery after Enzymatic or Microbial Treatment", "Journal of Fermentation and Bioengineering", 1998, pp. 495-501, vol. 85, No. 5, Publisher: Society for Biotechnology, Japan, Published in: doi:10.1016/S0922-338X(98)80068-8.
Torres, A. et al., "Application of two-phase slug-flow regime to control flux reduction on anaerobic membrane bioreactors treating wastewaters with high suspended solids concentration", "Separation and Purification Technology", 2011, pp. 20-25, vol. 79, No. 1, Publisher: Elsevier, Published in: http://www.sciencedirect.com/science/article/pii/S1383586611001560.
Tshiteya, Mukuna, "Fuel Production from a Brewery Residue", "Energy", 1985, pp. 1299-1306, vol. 10, No. 12, Publisher: Elsevier, Published in: doi:10.1016/0360-5442(85)90141-0.
Wen, C., et al., "Domestic wastewater treatment using an anaerobic bioreactor coupled with membrane filtration", Nov. 1999, pp. 335-340, vol. 35, No. 3-4, Publisher: Process Biochemistry, Published in: https://doi.org/10.1016/S0032-9592(99)00076-X.
Wilkie, A., et al., "Enhancement of Anaerobic Methanogenesis from Napiergrass by Addition of Micronutrients", "Biomass", 1986, pp. 135-146, vol. 11, No. 2, Publisher: Elsevier, Published in: https://doi.org/10.1016/0144-4565(86)90043-0.
Serna, Emmanuel, "Anerobic Digestion Process", 2009, pp. 1-3, Publisher: Waste-to-Energy Research and Technology Council.
Yu, H., et al., "Performance of an anaerobic filter treating soybean processing wastewater with and without effluent recycle", "Process Biochemistry", 2002, pp. 507-513, vol. 38, Publisher: Elsevier.
Baloch, M., et al., "The performance of a phase separated granular bed bioreactor treating brewery wastewater", "Bioresource Technology", Jul. 2007, pp. 1849-1855, vol. 98, No. 9, Publisher: Elsevier Ltd., Published in: doi:10.1016/j.biortech.2006.06.014.
Barlaz, M., et al., "Microbial, chemical and methane production characteristics of anaerobically decomposed refuse with and without leachate recycling", "Waste Management & Research", May 1992, pp. 257-267, vol. 10, No. 3, Publisher: ScienceDirect, Published in: https://www-sciencedirect-com.mutex.gmu.edu/search/advanced?docId=10.1016/0734-242X(92)90103-R.
Bochmann, G., et al., "Application of Enzymes in Anaerobic Digestion", "Water Science and Technology", 2007, pp. 29-35, vol. 56, No. 10, Publisher: IWA Publishing, Published in: doi:10.2166/wst.2007.727.
Doyle, J., et al., "Struvite formation, control and recovery", "Water Research", Sep. 2002, pp. 3924-3940, vol. 36, No. 16, Publisher: Elsevier Science, Ltd, Published in: https://doi.org/10.1016/S0043-1354(02)00126-4.
Fang, H., et al., "Anaerobic Treatment of Brewery Effluent", "Biotechnology Letters", Aug. 1989, pp. 673-678, vol. II, No. 9, Publisher: Kluwer Academic Publishers, Published in: https://doi.org/10.1007/BF01025281.
GB Patents Directorate, "Search Report for corresponding application GB120599.3 dated Jan. 21, 2013", Jan. 21, 2013, pp. 1-4, Published in: South Wales, UK.
GB Patents Directorate, "Search Report for the corresponding priority document GB1220608.2 dated Jan. 14, 2013", Jan. 14, 2013, pp. 1-4, Published in: South Wales, UK.
Ince, Bahar K., et al., "Assessment of Biogas Use as an Energy Source from Anaerobic Digestion of Brewery Wastewater", "Water, Air, and Soil Pollution", 2001, pp. 239-251, vol. 126, Publisher: Kluwer Academic Publishers, Published in: The Netherlands.
GP Patent Office, "Examination Report for Application #GB1413199.9", dated Sep. 22, 2014, pp. 1-7.
Japanese Office Action, "Corresponding Japanese Application No. 2015-542354, dated Nov. 27, 2017", , pp. 1-16.
Keenan, John D., and Iraj Kormi, "Methane Fermentation of Brewery By-Products", "Biotechnology and Bioengineering", 1977, pp. 867-878, vol. 19, No. 6, Publisher: John Wiley & Sons, Inc., Published in: DOI: 10.1002/bit.260190607.

(56) References Cited

OTHER PUBLICATIONS

Kida, K., et al., "Influence of mineral nutrients on high performance during anaerobic treatment of wastewater from a beer brewery", "Journal of Fermentation and Bioengineering", 1991, pp. 54-57, vol. 72, No. 1, Publisher: Elsevier, Published in: https://doi.org/10.1016/0922-338X(91)90146-8.

Kraemer, J., et al., "Continuous Fermentative Hydrogen Production Using a Two-Phase Reactor System with Recycle", Apr. 12, 2005, pp. 3819-3825, vol. 39, No. 10, Publisher: Environ. Sci. Technol., Published in: https://doi-org.mutex.gmu.edu/10.1021/es048502q.

\* cited by examiner

GRAIN PROCESSING

FIELD OF THE INVENTION

The present invention provides a process for producing biogas and/or methane from spent solid(s) material, including those derived from the production of alcohol from malt and grain distilling and/or fuel alcohol production. There is also provided a system for producing biogas and/or methane from solid(s) material such as derived from the production of alcohol from of malt and grain distilling and/or fuel alcohol production.

BACKGROUND TO THE INVENTION

Production of biogas from anaerobic digestion of energy crops such as maize silage or grass silage is a well established practise in Europe. Germany alone has over 7,000 anaerobic digesters operating largely on energy crops to produce biogas. Typically energy crops may have protein concentrations of between 8-15% (dry basis) making them suitable for anaerobic digestion. The biogas produced by this method of anaerobic digestion is typically used to generate electricity, steam and hot water via gas engines and waste heat boilers. Many of these installations are large scale and capable of generating between 20 and 40 MW electricity per hour. Government subsidies around the green electricity price make conversion of energy crops to biogas a real commercial proposition in both Europe and the UK.

Although such digesters have been employed for the digestion of energy crops waste material, little attention has been given to the waste products from distillery and other sources. Moreover, some industries, including distilleries have solid and liquid waste material and it would be desirable to be able to process both the solid and liquid waste material.

WO2102/001417 describes a process for the production of butanol or acetone from various initial distillery and/or brewery by-products, however, there is no suggestion of how to produce biogas and/or methane from the described starting materials. However, this patent application teaches that pot ale which is used in combination with draff should be diluted as it may contain inhibitory amounts of copper. Moreover, the patent application teaches that the carbohydrate source may require to be pre-treated by hydrolysing and/or applying enzymes. Moreover, when draff is digested in combination with pot ale, the patent application teaches that the draff is first pre-treated with acid and enzymes. Thus, the processes taught for co-fermenting carbohydrates, and draff in particular, with pot ale, are quite complex and labour intensive.

It is amongst the objects of the present invention to obviate and/or mitigate one of the aforementioned disadvantages.

SUMMARY OF THE INVENTION

The present invention is based on work carried out by the inventors into utilising waste products from a malt/grain distilling process in order to produce biogas/methane and optionally other commercially useful products. In particular the present inventors have been able to utilise a number of spent solid and optionally liquid by-products which are obtained during various distilling processes.

Thus, in a first aspect there is provided a process for producing biogas and/or methane, from the process comprising:
(a) providing a slurry comprising one or more solid spent cereal product(s);
(b) subjecting the slurry to an anaerobic digestion comprising methanogenisis at a pH of pH 6.6-7.6, in order to obtain a biogas and liquid digestate and optionally further processing the biogas in order to obtain methane.

It will be appreciated that the present invention can be run in a continuous or semi-continuous manner. That is new slurry material may be added continuously and digested, or batches of slurry may be added at particular time points.

The solid spent cereal product(s) typically comprise solid materials obtained from the production of malt and/or grain distilling, or distilling other materials, or from other processes including fuel alcohol production. A variety of spent cereal solid materials may be used including spent grains from grain distilleries, draff, brewer's grains, maize, and the like. In addition to the spent cereal, there may be a significant amount of proteinaceous material, such as yeast which has multiplied during a fermentation process. Indeed it may be desirable to have proteinaceous material, such as yeast present in addition to spent material which is rich in carbohydrate. Such spent solid materials may have relatively high protein values. For example, draff is approximately 22% dry basis protein and Vitagold® (a spent grain material, see below) may have up to 44% protein.

Grain distillery spent cereal solids are obtained from spent wash. This is the spent cereal and yeast slurry typically comprising around 5% total suspended solids that exits the base of the wash column of a continuous distillation plant or alternatively is the residue left after the wash pot still distillation from an all grains in mash process. The percentage suspended solids in spent wash are determined by the original gravity that the particular distillery is employing.

The spent wash material has a soluble solids component typically around 4%. The higher the original gravity the greater the suspended and soluble solids concentrations. A spent wash material comprising 5% suspended solids and 4% soluble solids would be typical for a grain distillery operating at 65 degrees original gravity.

The figures detailed above are based on a grain distillery operating with 9.0%-alcohol volume/volume wash feed to distillation. If however, the wash strength is higher then so too will be the suspended and soluble fractions in the spent wash.

The present inventors have shown that it is possible to anaerobically digest slurries which comprise such starting materials. Depending on any particular material and its protein/carbohydrate/fat amounts, it is possible to provide mixtures of starting materials in order to provide an optimum level of digestible substrates for anaerobic digestion. However, care has to be exercised to ensure the contents of the slurry are suitable for efficient anaerobic digestion and optionally generation of a liquid digestate possessing a high degree of bicarbonate alkalinity. For example, the present inventors have observed that when the solids in the slurry comprise a significant amount of protein (>than 20% dry basis protein), more micronutrient or antagonist addition may be required to facilitate the anaerobic process and biogas generation in as short a time as possible. Moreover, a high buffering capacity, or high level of bicarbonate alkalinity in the anaerobic digester may be required to neutralise any acidic products produced during the anaerobic process, such as when acidic feed stocks are utilised.

In a particularly preferred embodiment of the present invention, a high bicarbonate alkalinity or buffering capacity may be provided by way of utilising a starter culture obtained from another anaerobic digestion process, such as described in WO2013104911 (originally appended to specification of the priority application as an Appendix). A suitable starter culture/slurry (typically 3-10% v/v of the digester, such as 4-7% v/v) such as obtainable from the process(es) described in WO2013104911 will comprise a cocktail of microorganisms (including methanogens) suitable for anaerobic digestion of the material described herein, as well as a high buffering capacity. By providing a starter culture comprising a high buffering capacity as well as a cocktail of microorganisms, it has been observed by the present inventors, that additional pH control of the process may not be required. Thus, addition of the starter culture to the slurry may result in the required pH of 6.6-7.6 being attained, or an initial pH control may be required in order to reach the required pH range, but thereafter no further additional pH control may be required. Without being bound by theory, it is thought that the high buffering capacity is sufficient to start the anaerobic process and once started the process is self-sustaining. That is, once started, the anaerobic process continues to generate further bicarbonate alkalinity or buffering capacity such that addition of further slurry does not inhibit or harm the anaerobic process. The present inventors have observed that once started, they are able to continuously reintroduce fresh slurry to the process as the biogas and liquid digestate is removed. Thus, the present invention may be provided as a continuous process.

As observed by the present inventors individually certain solid waste products from distilling/brewing processes may not be the optimum starting source for anaerobic digestion and it may be desirable to mix a solid waste product from a distillery/brewing process with a second or further solid waste products in order to provide an improved digestible material. For example, it may be desirable to mix spent grains from a grain distillery with another distillery/brewing solid waste product or an agricultural waste product such as silage. Moreover, although silage has been used alone in anaerobic digesters, its combination with the spent cereal materials of the present invention may provide advantages in terms of the anaerobic process itself and/or a subsequent solid material resulting following anaerobic digestion.

Grain distillery spent cereal and spent yeast solids (suspended solids) are recovered from spent wash post continuous or pot still distillation by mechanical means. The dry matter content of the recovered spent grains and yeast from grain distilling will typically range between 28% and 40% dry solids subject to the mechanical separation device used. Typical mechanical devices for the separation of spent yeast and spent grain solids from spent wash are:

(a) Filter, membrane or belt presses.
(b) Decanter centrifuges.

The operational efficiency and percentage recovery of total suspended solids from the spent wash slurry will range from 70% for a decanter centrifuge to 98% for a filter press. The moisture content of the recovered spent grains will also vary with the type of mechanical device used for recovery. For example a decanter centrifuge will recover suspended solids from spent wash at circa. 28% dry substance whereas a filter may recover suspended solids from spent wash at up to 40% dry substance.

Normally, for grain distilleries the solid co-product is a wet solid, or the solid co-product may be combined with the concentrated soluble fraction (evaporated) following the initial mechanical separation and dried. The product has the general term distillers dried grains.

Trade names exist for the wet solid and dried co-products from grain distilleries. One such wet solid material is Vitagold® which is produced in the production of spirit alcohol from mainly wheat. The grain is mixed with malt and water in a pressure cooker type operation to release sugars from the cereal. Yeast is then added to ferment the sugars into alcohol. This is then distilled out of the mix at high temperatures with all the solids still in situ. The solids are then pressed to extract excess moisture leaving a friable, moist feed called Vitagold® Other similar materials to Vitagold® may be employed. The present invention therefore extends to spent wet solid and dried cereal products optionally in combination with spent yeast.

The composition of the wet and dry products is generally high in protein with a typical range of 38 to 44% dry basis protein, which is considerably higher than may be expected in relation to waste material from energy crops. The yeast fraction recovered by mechanical means is the main reason for the high protein content. Non-fermentable carbohydrate and oil are also key macromolecular components in the make up of the solid co-product fraction.

Draff is the spent cereal solids residue remaining following the mashing process which is carried out for both Scotch Malt Whisky and Irish malt whiskey, as well as malt whisk(e)y produced in other geographical locations and also following beer mashing of malt mash. The main constituents of draff at a macromolecular level are non-fermentable carbohydrates such as hemicelluloses and cellulose together with oils and protein. Moreover, the overall composition of draff is likely to be relatively constant over time, which potentially makes it a suitable substrate for anaerobic digestion. The C:N:P ratios given the macromolecular make up are also likely to be in an acceptable range for anaerobic digestion. Typically draff has a high moisture content, such as 75%-80% wt/wt and is acidic in nature, typically pH 4.0-5.5. Also, draff being a solid does not make it directly readily digestible over a short time period. Solids may be anaerobically digested, but in order to be commercially viable it is important that digestion and hence biogas production occurs in a short as time as possible. Surprisingly, the present inventors have observed that the use of enzymes, such as cellulases and hemi-cellulases, does not improve the digestion of draff and other spent cereal material and as such the present invention may be conducted substantially in the absence of specifically added enzymes, such as hemi-cellulases and cellulases. This of course does not exclude any enzymes which may be naturally present in the starter culture and/or liquid digestate.

Typically the moisture content and ash content of the solid product(s) draff is measured in the first instance. For a solid product starting material, any biogas or methane yield results require to be expressed in terms of x m3 (biogas or methane) per tonne volatile dry solids.

The slurry is provided by mixing the solid(s) with a liquid or liquids to produce a slurry with a dry solids content of up to 20% on a wt/wt basis, although typically the slurry will have a lower total solids content of up to 15%, typically up to 12%, 10% or less. The liquid or liquids may include spent pot ale, or a diluted pot ale syrup which remains following a malt whisk(e)y distillation process, water and/or optionally a liquid which possesses a high buffering capacity for maintaining the slurry at the desired pH. The pH of the slurry may be between pH 3.5 and 8.0, for example. Desirably the slurry may have a high alkalinity (typically bicarbonate alkalinity), capacity, although this is not essential. A particularly preferred liquid may be a digestate obtained from anaerobic digestion of soluble waste products from a process as described in WO2013104911, or is a liquid digestate, wherein the bulk of the suspended solids have been removed, as obtained in accordance with the present invention, which is recycled and used to form a slurry with fresh spent cereal product(s).

In a further aspect there is provided a system for digestion of a substantially aqueous solution, or aqueous and oil two phase system and digestion of one or more solid spent product(s), they system comprising a first anaerobic reactor for anaerobically treating said substantially aqueous solution or aqueous and oil two phase system, so as to produce biogas and a liquid digestate with a high level of bicarbonate alkalinity and a second anaerobic digester for anaerobically digesting one of more solid spent product(s) (as defined herein) which are provided to the digester in the form of a slurry comprising said one or more solid spent product(s) and said liquid digestate from the first anaerobic reactor.

Liquid digestate from the first anaerobic reactor may be used to form the slurry at the start up of the second anaerobic digestion, until such time as a high level of bicarbonate alkalinity has built up in the second anaerobic digester, whereupon liquid digestate from the second anaerobic digester can be recycled in order to make fresh slurry for introduction to the second anaerobic digester.

Pot Ale is the residue left after the wash distillation in the production of Scotch or Irish Malt Whisk(e)y. This stream would represent approximately two-thirds of the original wash (beer) used to charge the wash still. The pot ale composition is made up of both soluble solids and suspended solids with the latter dominated by spent yeast. The soluble solids derived from pot ale syrup are dominated by non fermentable carbohydrate together with some oils, organic acids, trace ethanol and protein. The total solids component of pot ale would generally be around 4.5% on a wt/wt basis (Total Solids=Soluble Solids+Suspended Solids).

The chemical oxygen demand of pot ale would typically lie in the range of 60,000 to 65,000 mg per litre for a distillery operating with 9% alcohol volume/volume wash (typical for a malt distillery). Ultimately the pot ale COD is determined by the beer strength that any specific malt distillery will operate at. Higher beer strengths will result in higher COD concentrations in the pot ale. Beer strength in malt distilling may be as high as 11% alcohol volume/volume and consequently provide a higher concentration of COD in the pot ale.

Pot ale syrup is simply pot ale that has been concentrated in an evaporator. The original 4.5% total solids may be concentrated to between 35 and 45% dry solids subject to the viscosity of the pot ale syrup and type of evaporator used in the process.

The evaporated fraction is known as foul condensate and contains some of the volatile components of the pot ale such as trace ethanol and acetic acid. The evaporated fraction or foul condensate as it is known is low in COD (typically 1,000 to 2,000 mg/litre) and is normally treated in a biological treatment plant to remove this COD. A similar material to pot ale syrup obtained from malt distilleries may be obtained from grain or other cereal distilleries. Such a material may be obtained by concentrating, typically through evaporation of a decanter light phase or thin stillage as known in the art. Such a concentrated material may also be used in accordance with the present invention.

The chemical oxygen demand of pot ale syrup at 45% dry solids would typically lie in a range of 580,000 to 630,000 mg per litre. (based on evaporator increasing concentration of pot ale ×10 minus loss of some COD to foul condensate). The COD loss to foul condensate is trace ethanol and acetic acid. However, the protein concentration is relatively high at around 32-37%.

Advantageously the present inventors have found that they are able to employ pot ale syrup or other concentrated syrup in generation of a suitable slurry material, which saves on costs and physical sizes of the digesters. The amount of pot ale before making the syrup, is quite substantial and if this is employed in making the slurry, the volumes required to be digested become extremely large and so more digesters may be required, hence the increase in costs. However, by reducing the volumes required by employing a diluted pot ale syrup in place of pot ale as received from the distillation, cost savings can be realised. The present inventors have been able to feed pot ale syrup at 45% dry solids combined with draff, in the amounts obtained from a single distillery, directly into a single digester. It is also possible to utilise more pot ale syrup which may be derived from other distilleries, saving on the costs by reducing the numbers of digesters which may be required. For example, this may be an equivalent malt distillery ratio of one of draff and two distilleries of pot ale syrup on a 35 day retention time. Although the use of pot ale syrup may have been desired, the chemical make-up of the pot ale syrup and especially the high protein and potassium levels may have inhibited the digestion process from proceeding optimally. However, the present inventors have nevertheless successfully carried out digestion of draff or other spent cereal material with diluted pot ale syrup. Without wishing to be bound by theory, the digestion of pot ale syrup and draff, which both have high protein levels, may lead to the production of ammonia and consequently ammonia ions, which would likely be inhibitory. However, the high potassium levels which may have been expected to act as an inhibitor to the anaerobic process, can in fact serve to off-set, or antagonise the effect of the ammonium ions, such that the anaerobic process can continue very satisfactorily. Thus, the efficient anaerobic digestion of spent grain material in combination with pot ale or pot ale syrup is quite unexpected. Moreover, by employing pot ale or other syrup, liquid digestate from the digester itself and/or from another anaerobic digester can be used in order to make the initial slurry to the desired solids concentration. Advantageously, this allows high-bicarbonate alkalinity to be provided to the slurry, whilst also serving to bring the slurry to the desired pH.

However, the impact of any additional acidity derived from liquid(s) such as pot ale/pot ale syrup in the slurry must be considered. As mentioned above, the pH of the anaerobic process must lie between the desired pH ranges and hence pH adjustment may be required as necessary. The residual bicarbonate alkalinity must also remain above 3,000 mg per litre and up to 9,000 mg per litre, ideally between 4,000 and 5,000 mg/l such as calcium carbonate. The level of acidity in the pot ale syrup can be very variable and even when employing a digestate with a high bicarbonate alkalinity, as will be described, a small pH adjustment with alkali may be required to meet the required pH and bicarbonate alkalinity conditions required for an efficient anaerobic fermentation in the digester.

This term high level bicarbonate alkalinity is understood to relate to be at least 3000 mgl$^{-1}$ (typically 4000 to 5000 mgl$^{-1}$, expressed in terms of mgl$^{-1}$ of calcium carbonate, and can be calculated as follows:

Bicarbonate alkalinity (as mgl$^{-1}$ calcium carbonate)=Total Alkalinity (mgl$^{-1}$ CaCO$_3$)−Total Volatile Fatty Acids (ppm)×0.71

The total alkalinity may be determined by titration to pH 4.0 using 0.1 N hydrochloric acid. The total Volatile Fatty Acids may be determined by gas chromatography.

Where the liquid or liquids used to form the slurry includes a liquid with a high (e.g. bicarbonate) alkalinity capacity, it may not be necessary to adjust the pH in the anaerobic digester, as it may be in the required pH range. However, if the mixture in the anaerobic digester is not within the desired pH range of pH 6.6-7.6, more preferably pH 7.0-7.4, then the pH may be adjusted by the addition of an appropriate alkaline material, such as lime (i.e. calcium oxide or calcium hydroxide, or sodium bi-carbonate. Desirably such an adjustment may only be required at the start of the anaerobic digestion as a build up of bicarbonate alkalinity may occur during the anaerobic process and the desired pH level attained naturally. That is, the present inventors have observed that following an initial start up, where the pH may require to be adjusted and/or a liquid digestate high in bicarbonate alkalinity from another anaerobic process may be employed, the mixture in the anaerobic digester may build up its own high level of bicarbonate alkalinity. Once this occurs, liquid digestate obtained from the digester can be used to make fresh slurry which itself will have a high level of bicarbonate alkalinity and may not require further pH adjustment.

Anaerobic digestion is typically carried out by mesophillic acidogenic and methanogenic bacteria operating in symbiosis to produce biogas which typically comprises methane and carbon dioxide. A starter culture of microorganisms for carrying out an anaerobic digestion may be obtained commercially, from suppliers operating conventional anaerobic processes, such as sewage sludge treatments. On application of the process conditions the culture of microorganisms becomes adapted, with organisms finding the conditions advantageous growing at the expense of those finding the conditions adverse.

Alternatively, the acidogenic and methanogenic bacteria may be obtained from another anaerobic process where a suitable mixture of organisms have been developed during the anaerobic process. One such process is described in WO2013104911 which describes a process developed by the present inventors for anaerobically digesting soluble waste products from distilleries, for example and which generates a conditioned mesophilic methanogenic sludge blanket over time. A sample of this sludge blanket may be used as a starter culture for use in the anaerobic process of the present invention.

Appropriate heating of the slurry may be provided to maintain the slurry at the desired temperature for mesophilic anaerobic digestion by mesophilic acidogenic and methanogenic bacteria of between 30° C.-40° C., typically 36-38° C., although typically this may not be required and temperate and warmer climatic zones, or may only be required in colder months of the year.

Typically average retention time of the slurry in the anaerobic digestion phase (in order to obtain at least 75% digestion of the solids material in the slurry) is of the order of 30-70 days such as 30-45 days, especially 32-37 days. However, the present inventors have observed that when conducted in accordance with the present invention a significant amount [approximately 50%] of the total biogas production occurs within 3-7 days of slurry addition and as such much shorter average slurry retention periods, such as less then 15, 12, 10, or even 8 days may be appropriate and commercially viable. However, desirably the retention period may be such that an anaerobic digestate with a residual methane content of less than 1 m$^3$ methane per tonne VSS is obtained per day on a residual gas test.

Preferably the solids material or slurry, prior to anaerobic digestion is subjected to a milling or other suitable grinding or homogenising process in order to reduce the particle size, increase surface size area, and/or aid solubilisation of the solids in the slurry. Desirably the solids particles/material in the slurry should have an average maximum diameter/axis of less than 0.5 mm, preferably less than 0.2 mm. It is understood that some of the initial solid material present in the slurry will become solubilised prior to anaerobic digestion and be capable of being anaerobically digested. However, further solubilisation of the solids present in the slurry will occur during the anaerobic digestion. Without wishing to be bound by theory, it is thought that the bacteria which carry out the anaerobic digestion release enzymes such as cellulases and hemicellulases which facilitate further breakdown and solubilisation of the solids present in the slurry. This may be why addition of exogenous enzymes is not generally required or necessary in the present invention. Advantageously when a liquid digestate with a high bicarbonate alkalinity from another anaerobic digestion process and/or liquid digestate obtained from the process described herein are employed, this may facilitate rapid solubilisation of the solid(s) material as the above described enzymes will be present.

Monitoring of micronutrient levels and addition of micronutrients to the anaerobic digestion process may also be carried out according to the invention, as will be described in more detail below. This may be particularly important when the suspended solids in the slurry includes a significant (such as >than 20% protein on a dry basis) amount of protein. As mentioned above, it may also be expected that ammonia and ammonium ions may be produced from the protein material and this can be monitored and antagonistic material, such as calcium or magnesium ions may be provided to off-set the likely inhibitory effect of ammonia/ammonium ions.

An optional "acidogenic" phase may be employed prior to the anaerobic digestion at pH6.6-7.6. Such a phase typically runs at acid pH in the range of 3.5 to 5. A pH in the range of 3.5 to 4.2 has been found to assist in allowing acidogenesis/acetogenesis to occur, thereby increasing levels of VFAs passed forwards to the subsequent anaerobic stage at 6.6-7.6. However in practice the anaerobic stage at pH6.6-7.6 has been shown to be capable of processing VFAs i.e. acetogenesis occurs to produce acetic or other small chain carboxylic acids. Thus, advantageously, in some embodiments of the present invention, an acidogenic phase is not employed. It will be appreciated that such an acidogenic stage if conducted, is conducted on the slurry prior to the pH being made or adjusted to pH6.6-7.6.

If required the slurry may be adjusted to an acid pH as required before it is processed in an acidogenic reactor. In general, where an acidogenic reactor is employed the acidogenic process is relatively fast with a typical hydraulic retention time of only circa 24 hours (with no recycling). Typically the acidogenic stage is carried out with mixing in the acidogenic reactor.

For any acidogenic stage carried out before the anaerobic stage appropriate microorganisms can be found ubiquitously in the environment, especially in the (nutrient rich) aqueous effluent streams contemplated as feedstock for spirits drinks processes which can produce rapid growth of these organisms e.g. up to 0.15 kg per kg of COD removed.

Typically the anaerobic process is carried out in an enclosed tank or lagoon comprising a mixture of methanogenic and acidogenic microorganisms. In a preferred embodiment the tank or lagoon comprises an a first portion where the majority of the anaerobic process is carried out and a separate "holding" portion which retains a digestate liquid following initial anaerobic digestion in the first portion and where further anaerobic digestion may occur. Desirably the average retention time in the first portion is between 30-40 days, such as between 32-37 days, typically around 35 days.

Advantageously the liquid digestate from the anaerobic and/or holding portions is not recycled, other than some/a portion of the liquid digestate being used to form further slurry comprising the fresh solid material. The liquid digestate obtained following anaerobic digestion is expected to have the desired high (bicarbonate) alkalinity and hence can impart the correct pH and buffering capacity to further slurry.

High bicarbonate alkalinity levels which develop during anaerobic digestion are also expected to reduce the build up of inhibitory levels of by-products such as propionic acid in the anaerobic reactor. High propionic acid levels (and the level of other undesired species such as ammonia and $H_2S$) result in much reduced quality of biogas and reduction in COD breakdown.

Furthermore, with a natural high bicarbonate alkalinity developing during the anaerobic process, the mixture in the first portion readily maintains the desirable pH (pH 6.6-7.6, preferably pH 7.2 to 7.4) because of the very large reservoir of alkalinity present. This can avoid any requirement to continually adjust pH with added alkalinity. Adjustment of pH may be required when operating an optional acidogenic stage as the output from a preceding acidogenic reactor may have a low pH e.g. at about 3.5.

The anaerobic and holding portions produce biogas and liquid digestate. The biogas produced (which is generally methane and carbon dioxide, although may include minor amounts of other gases, such as hydrogen sulphide) can be used as a fuel for heating for example, or used in a gas engine to provide electricity and heat. Alternatively the biogas can be "cleaned up" in order to reduce the amount of carbon dioxide, water, hydrogen sulphide etc, in order to provide methane (>98%) which may be supplied directly to the gas grid. Such "clean-up" processes are well known in the art and include gas scrubbing (see for example Kapdy, S. S. et al, Renewable Energy (2004) p 1-8).

The liquid digestate typically includes phosphorous, nitrogen and potassium, which may be present in a variety of forms and may include struvite (magnesium ammonium phosphate). However, as well as being used to form the slurry with new solid material the liquid digestate may be further processed for use in agriculture. Processing of the liquid effluent following anaerobic digestion may include evaporation to a concentrate for use as a liquid fertiliser or evaporation to a solid product e.g. by spray drying.

As mentioned above it may be desirable to add micronutrients during the anaerobic digestion, especially at least one metal salt comprising one or more of cobalt, nickel, and iron, can also produce significant benefits. Selenium may also be employed as an added micronutrient. Other micronutrients such as vitamins, for example riboflavin, vitamin B12 may be appropriate. Advantageously a salt of each of cobalt, nickel and iron is added, with selenium also added as required. Typically metal salts are provided in the form of a chloride or sulphate salt.

It has been found that improvements in maintenance of the biomass and in the quality of the process output are achieved by monitoring the micronutrient content (preferably by an accurate analytical method, such as ICP—inductively coupled plasma mass spectroscopy—measurements) and adding measured amounts of micronutrients. Both the monitoring and/or the additions of the micronutrients may be done automatically if desired. Monitoring can avoid overdosing of a micronutrient, some of which are inhibitory/toxic to anaerobic microorganisms when in excess.

Other monitoring of the anaerobic digestion can be advantageous, for example using an Oxidation-Reduction Potential probe (ORP probe) to measure oxidation-reduction potential within the methanogenic stage. This measurement provides indication that the process is operating correctly in an anaerobic fashion. Typically if the measurement is of the order of −350 mV to −530 mV then the process is operating in favourable conditions. If the measurement drifts from such a value then less favourable conditions for the production of methane are present.

As far as the measurement of micronutrient content is concerned it may be made following obtaining samples (manually or automatically) from the methanogenic stage itself. Advantageously and conveniently the monitoring of the content of a micronutrient in a methanogenic stage is not determined from sampling the content of the anaerobic stage itself but is determined by measuring the micronutrient level in the input to the process or to the anaerobic stage and also in the output from the anaerobic stage and comparing the two results in conjunction with an understanding of the expected growth of microorganisms in an efficiently operating process.

When operating the anaerobic process, it may be that the levels of measured micronutrient in the input and in the output can be comparable in content, indicating that the micronutrient in the feed is not readily bio-available to the microorganisms, which would be expected to consume the micronutrient as they grow, reducing the amount found in the liquid output. For this reason adding micronutrients as a supplement, typically on a daily basis or less frequent but regular basis in response to monitoring results, has been found beneficial. With a smoothly running process and a relatively consistent feed the monitoring steps do not need to be carried out frequently, but additions on a daily basis or other regular (such as weekly) basis keeps the micronutrient levels within the desired concentrations.

Typical in cell "target" amounts of micronutrients can be found in the literature for anaerobic processes, for example the metals required to sustain a healthy culture of microorganisms. For example, Iron—1,800 mg $kg^{-1}$. Nickel—100 mg $kg^{-1}$ and Cobalt—75 mg $kg^{-1}$. (on a dry weight of sludge basis). For selenium smaller amounts are indicated, typically less than 50 mg $kg^{-1}$.

DETAILED DESCRIPTION

The present invention will now be further described by way of example and with reference to the attached figure which show:

Figure 1:
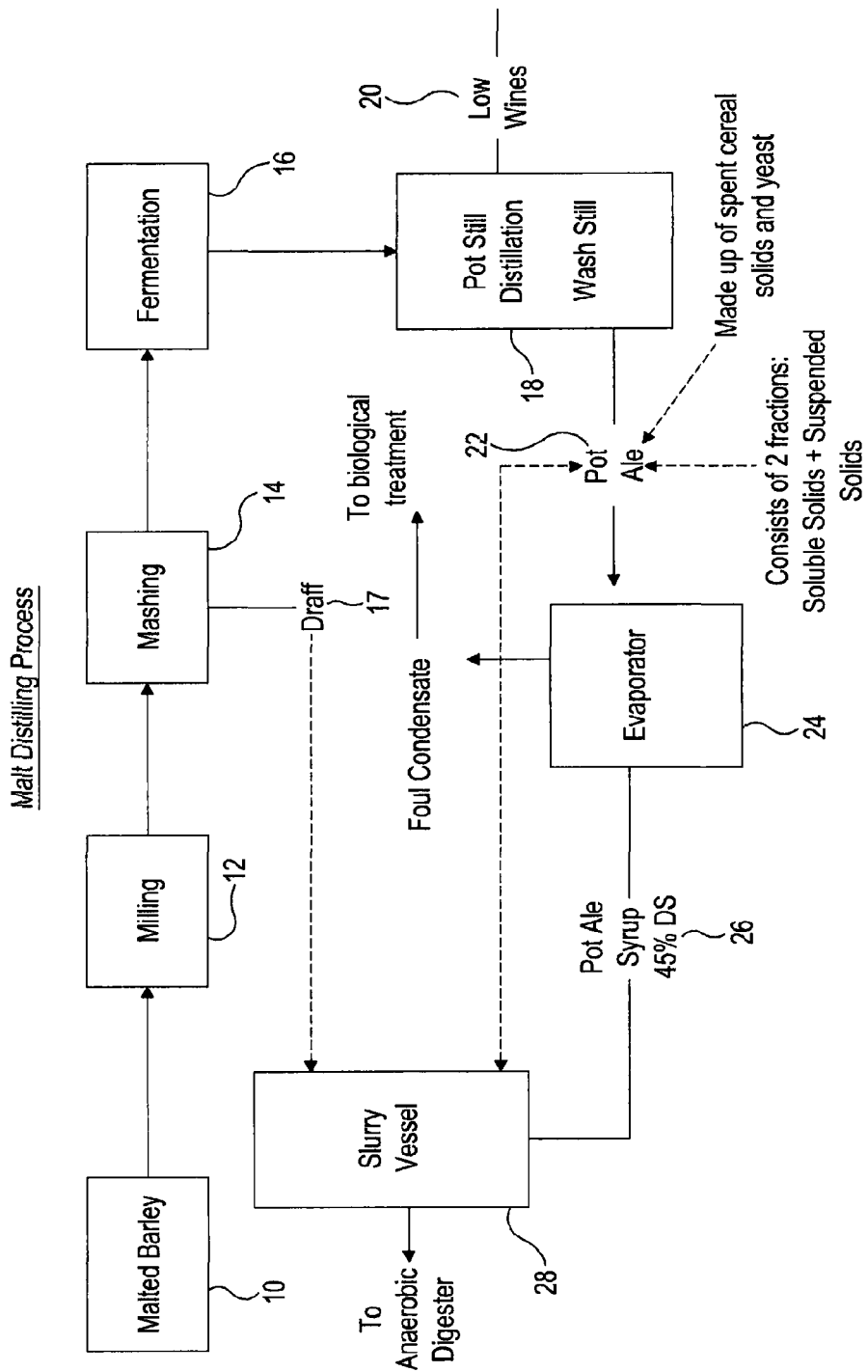
FIG. 1 shows a schematic diagram of the malt distilling process and where draff and other waste materials may be derived and used in the present invention.

FIG. 1 shows a schematic diagram of the malt distilling process. As can be see malted barley (10) is initially milled (12) before subjecting the milled malted barley to a mashing process (14). Following mashing, draff (16) is removed and the resulting liquid is subjected to fermentation (16). After fermentation, the resulting liquid is distilled (18) and the low wines fraction (20) separated for further distillation. The liquid remaining in the still is pot ale (22) which includes trace spent cereal solids and yeast, which may be in form of soluble solids or suspended solids. The pot ale (22) may be used directly to form a slurry comprising draff, or may be subjected to an evaporation process (24), in order to make pot ale syrup (26) and foul condensate (28), which can be further processed. Pot ale syrup (26) can be used to form slurry comprising draff, within a slurry vessel (28). The resulting slurry can be subjected to an initial acidogenic process, or directly to an anaerobic process to make biogas and liquid digestate.

Figure 2:
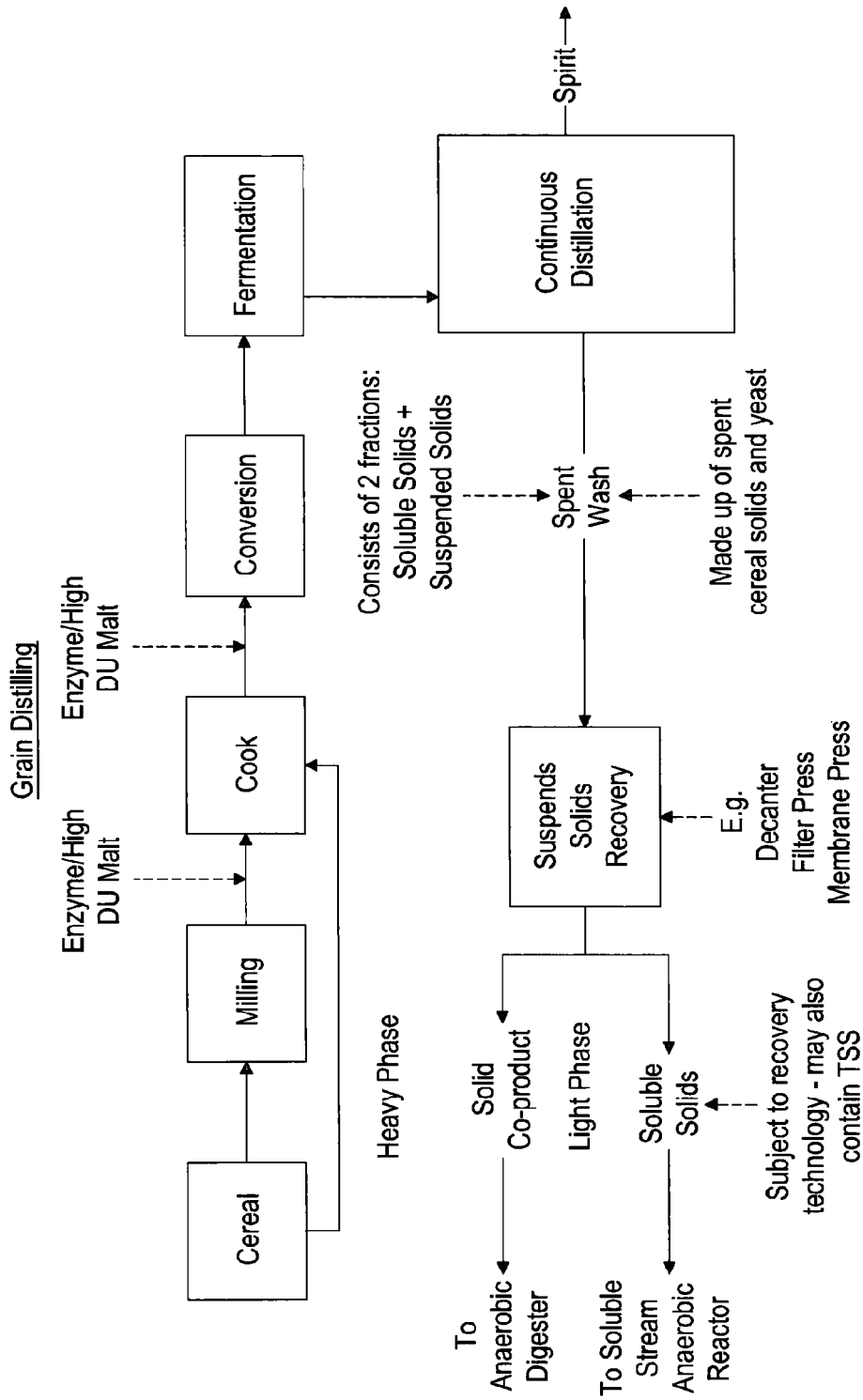
FIG. 2 shows a schematic diagram of a grain distilling process and where solid waste products may be derived and used in the present invention.

FIG. 2 shows schematically the essentials of a grain distilling process. The spent wash includes a soluble fraction and suspended solids which comprises spent cereals and yeast.

The suspended solids may be recovered by decanting, filter pressing, membrane pressing, belt pressing or the like and the solids material comprising spent grain and yeast may be use in the present invention.

Figure 3:
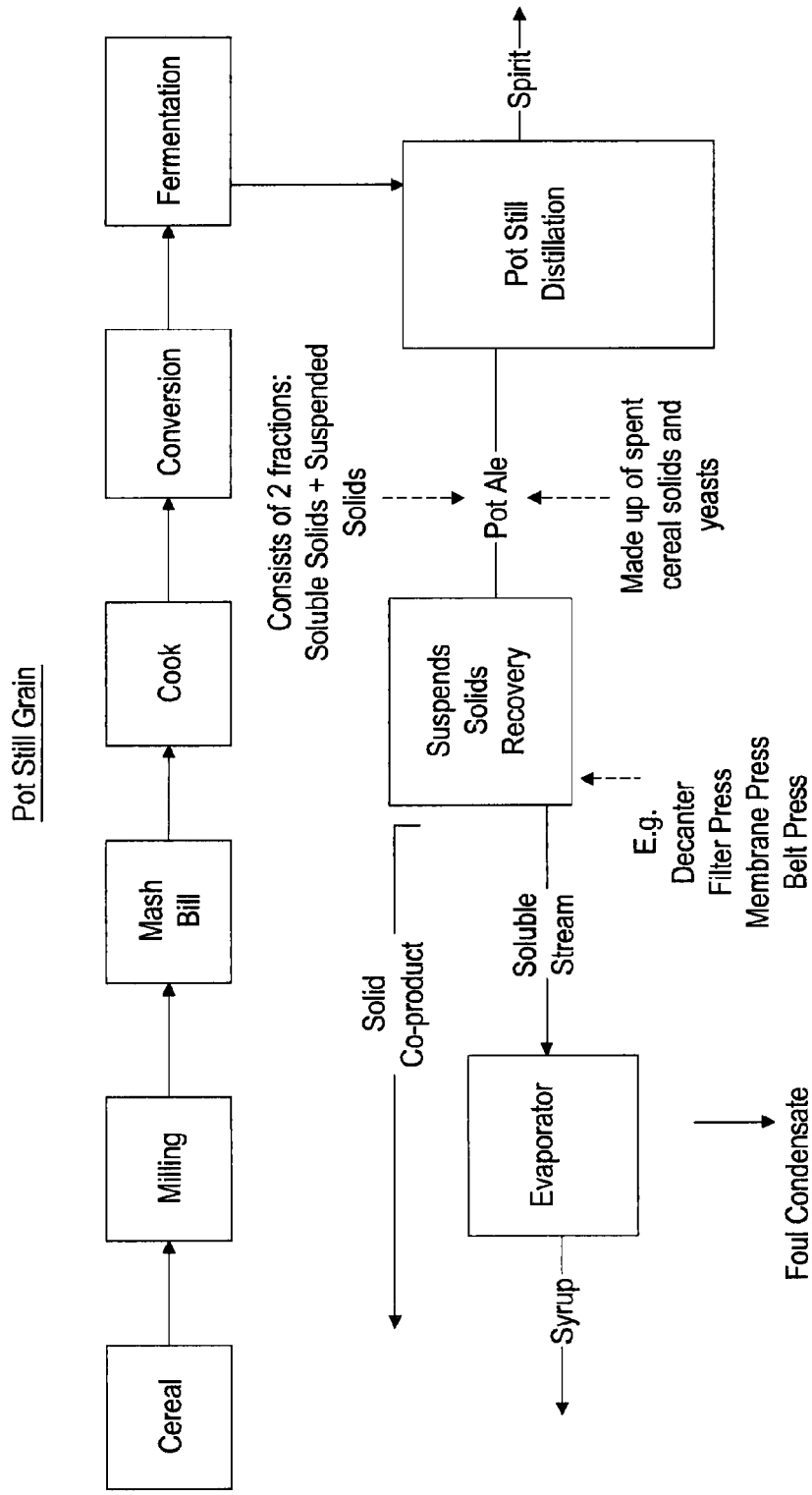
FIG. 3 shows a schematic diagram of a pot still all grains in distilling process and where solid waste products may be derived and used in the present invention.

FIG. 3 shows schematically the essentials of a pot still all grains in distilling process. Following pot still distillation, pot ale is removed and this pot ale includes soluble dissolved solids as well as suspended solids which comprise trace spent cereal solids and yeast. Akin to the grain distilling process described above, the suspended solids may be recovered by decanting, filter pressing, membrane pressing, belt pressing or the like and the solids material comprising spent grain and yeast may be use in the present invention.

Figure 4:
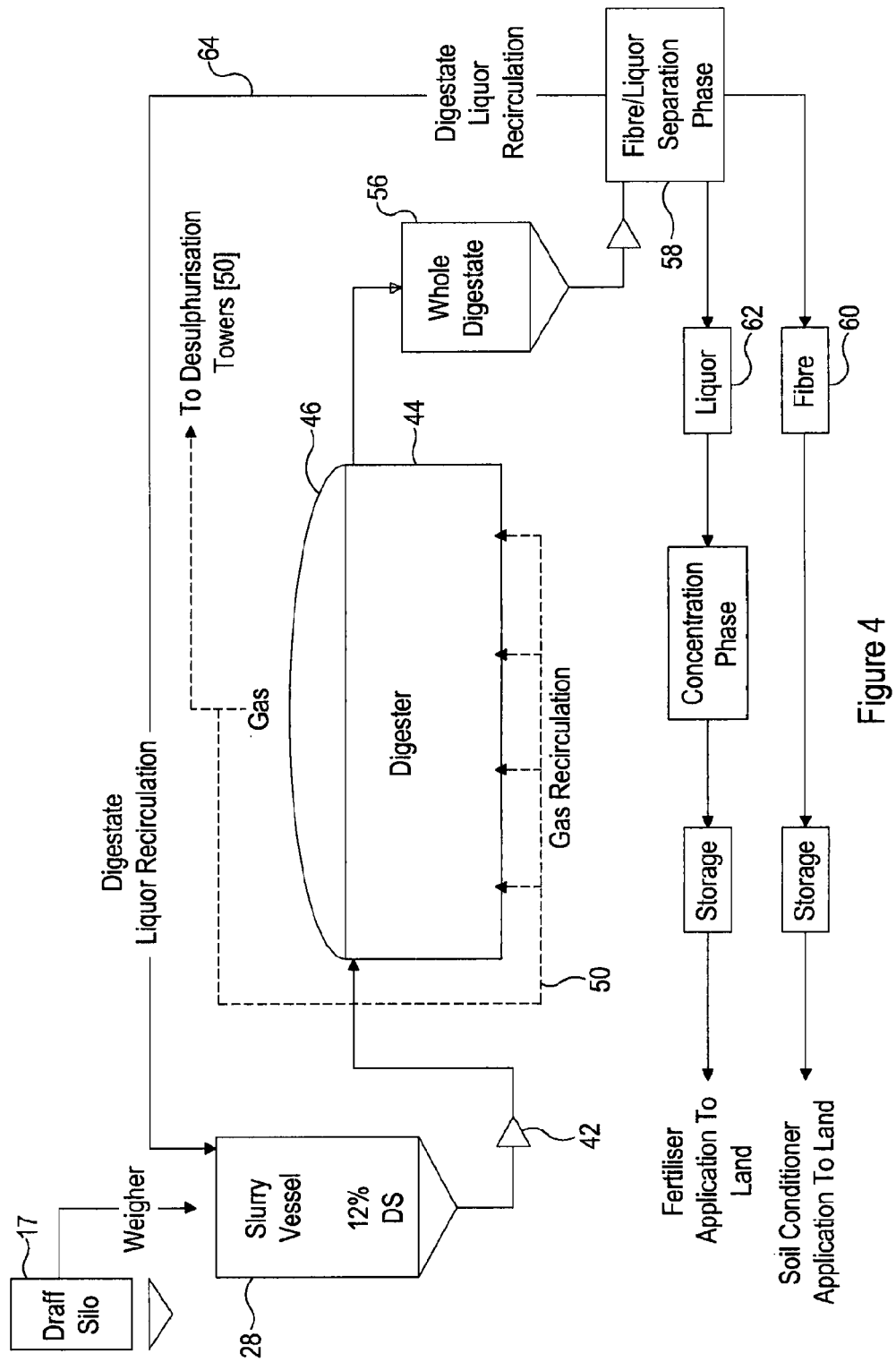
FIG. 4 shows a schematic diagram of a solid(s) digestion process in accordance with the present invention.
Figure 5:
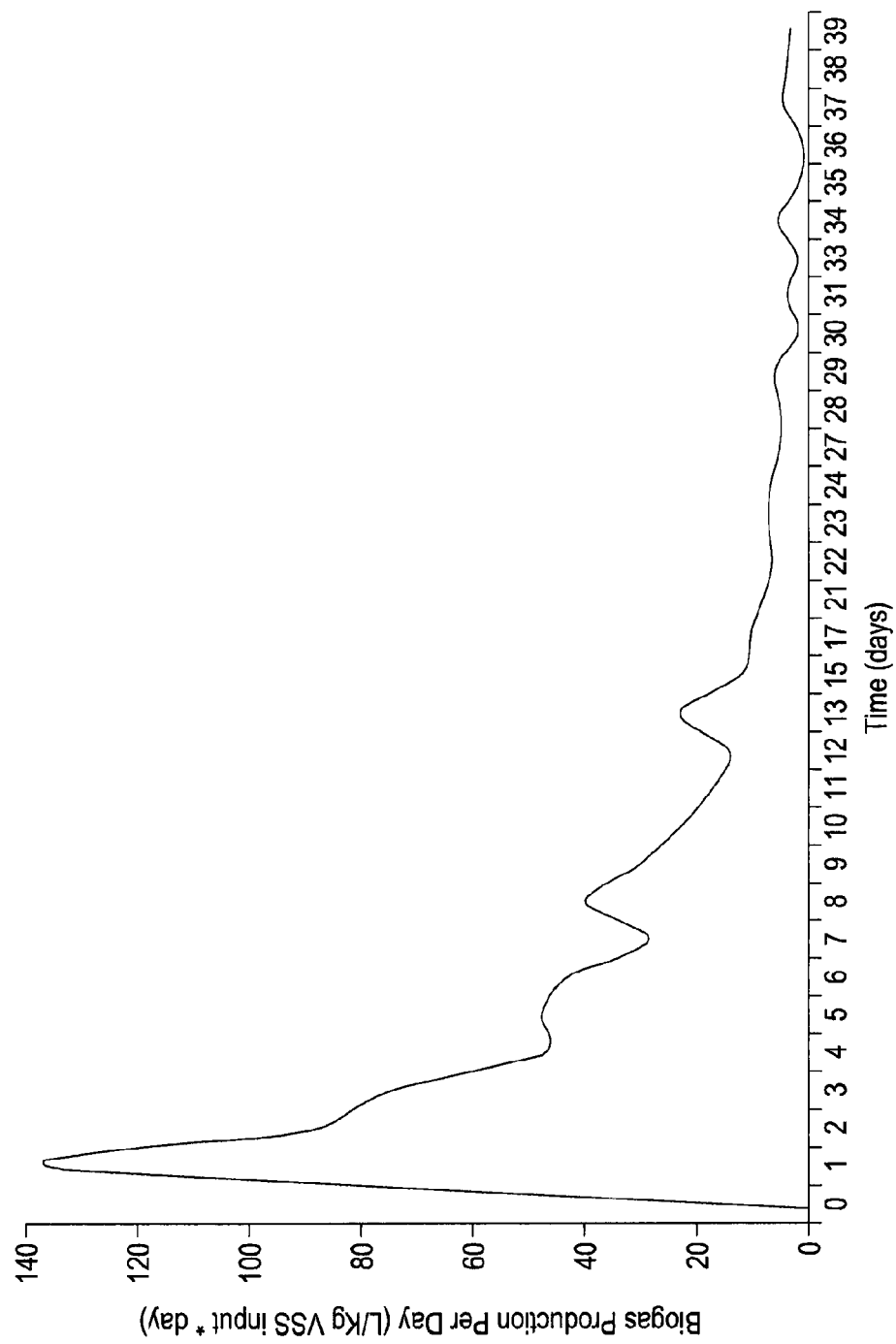
FIG. 5 shows the results of biogas production over time carried out by a process according to the present invention.

FIG. 4 shows schematically an example of a process in accordance with the present invention. Draff (17) is initially mixed in a slurry vessel (28) with high bicarbonate alkalinity anaerobic digestate (effluent stream from an anaerobic reactor or digester, see for example the attached appendix), pot ale (22) and/or pot ale syrup (26) to produce up to a 12% dry solids slurry on a wt/wt basis. The slurried draff then undergoes a reduction in particle size by mechanical means (42) to increase surface area and solubilisation rates in the anaerobic digester.

By high bi-carbonate alkalinity digestate we mean digestate with a bi-carbonate alkalinity between 4,000 and 5,000 mg per litre expressed as calcium carbonate.

Following particle size reduction the slurried draff is transferred to a digester vessel (44) and starved anaerobic sludge (taken from conditioned sludge prepared in accordance with the process described in WO2013104911) is added to start the anaerobic conversion process to biogas and liquid digestate. The digester vessel (44) is closed and contains an internal deformable gas hood (46), which expands within the vessel upon biogas production and evolution from the slurry.

The starved anaerobic sludge was taken from an existing anaerobic reactor working on distillery spent solubles. Sludge addition rate is typically 5% of the total working volume of the digester. The sludge dry solids are measured for each experiment and are found to be approximately 3% dry solids.

The operation is carried out under mesophilic conditions with digester maintained at 37 degrees centigrade+/−2C for the duration of the experiment. Some of the gas which is evolved is recirculated (50) in order to facilitate mixing of the slurry within the digester vessel (44).

The anaerobic digestion process experiments are typically run for 35 days and both biogas and methane yields per tonne volatile dry substance are calculated.

Gas which is collected can be sent to desulphurisation towers (50) to remove hydrogen sulphide, before being used to run a gas engine in order to produce electricity, or further cleaned in order to remove carbon dioxide and to provide clean methane which can be supplied directly to the national grid, for example, or as an alternative to scrubbing towers some oxygen may be introduced to the headspace of the digester to react with $H_2S$ and produce elemental sulphur.

The liquid residue remaining after anaerobic digestion is known as whole digestate and can be transferred to a whole digestate vessel (56) This whole digestate may be separated further by mechanical means or filtration (58) into a solid fibre stream (60) and liquor (62), a portion (64) of which (being high in bicarbonate alkalinity) can be recirculated back to form new slurry.

The remainder of the separated liquor digestate, which is the major portion, can be concentrated in order to provide a solution with desired levels of Na, K, P, for application to the land as fertiliser. The solid fibre portion can be applied to land as a soil conditioner, for example.

Where filtration is used a partial suspended solids separation takes place followed by ultrafiltration and reverse osmosis. The retentate streams are richer in N:P:K as a result of concentrating up these fractions by filtration.

Alternatively evaporation is also an option. Here the pH of the digestate should be adjusted to around pH to 5 to hold ammonium in solution for the evaporator process, otherwise this will lost as ammonia to the foul condensate fraction.

Similar small scale experiments were carried out using 10 litre glass digester vessels with gas tubes leading to graduated water column collection vessels, where both total quantity of biogas and methane can be accurately measured. The experimental work for yield determination was typically carried out in duplicate digesters with a third digester operating on the same substrate that is used to examine the internal chemistry of the anaerobic conversion process. These experiments are repeated to ensure yields and rate of gas production can be replicated.

EXPERIMENTAL

The key steps in the experimental protocol are outlined as follows:

1. Grain Distilling Spent Solids Preparation for Laboratory Anaerobic Trials
   (a) A sample of distillery spent grain comprising spent cereal solids and yeast is recovered from the heavy phase of distillery spent wash separation via: by decanter centrifuge or filter press or membrane press.
   (b) The spent grains sample is checked for moisture content and ash content.
   (c) The percentage volatile suspended solids dry basis is then calculated.
   (d) The distillery spent grains sample is made up to a 12%-20% dry solids slurry using digestate from an existing soluble stream anaerobic reactor or liquor stream from an anaerobic digester that is rich in bi-carbonate alkalinity and provides a natural slurry pH in range of 7.2-7.4. Note, that the bi-carbonate alkalinity of the digestate or liquor must lie in the range of 4,000-5,000 mg/litre expressed as calcium carbonate.
   (e) Alternatively if no digestate or liquor is available the sample may be made up to a 12%-20% dry solids slurry with water and pH adjustment by lime or sodium bi-carbonate to pH 7.2-7.4.
2. Milling of Grain Distilling Spent Solids
   (a) The slurry is then milled using a stick blender to reduce the particle size of the solids present.
   (b) Particle size reduction using the stick blender is carried out for 5 minutes per sample.
3. Anaerobic Sludge
   (a) Anaerobic sludge is sampled from an existing anaerobic reactor and stored under ambient conditions for a period of one week. The purpose of storage phase is to starve the sludge.
   (b) This is the seed sludge that will be added to the spent grains solids slurry.
   (c) The seed sludge dry solids are measured and are typically 5% suspended solids on a dry basis.
4. Anaerobic Fermentation—Biogas Volume and Methane Concentration
   (a) The distillery spent cereal solids slurry and sludge in pre-determined quantities are added to 10 litre glass anaerobic digesters.
   (b) The 10 litre glass digesters are placed in a water bath operating at a controlled temperature of 37 degrees centigrade.
   (c) The digester gas collection headspace is in turn connected to graduated water columns so that the biogas volume can be measured each day.
   (d) There is an additional connection from the digester that allows the carbon dioxide and methane content of the biogas to be determined.
   (e) Apart from total biogas volume and gas composition this method also allows the rate of gas production and methane production to be determined.
5. Anaerobic Fermentation Time
   (a) The anaerobic fermentation is allowed to run for a period of 35 days.
6. Evaluation of Biogas and Methane Yield
   (a) The total biogas volume collected is expressed as "x m3 biogas per tonne volatile dry solids."
   (b) The total methane volume measured is expressed as "Y m3 methane per tonne volatile dry solids."
7. Whole Digestate
   (a) The N:P:K values of the whole digestate are measured after 35 days anaerobic fermentation.

Biogas volume and gas quality (averaging 60% methane, 40% carbon dioxide and trace $H_2S$ typically 300-700 ppm$H_2S$) were measured on a daily basis throughout the duration of the experiment. The third digester was used to determine the internal chemistry via soluble COD, VFA, bi-carbonate alkalinity and pH. After 35 days anaerobic fermentation the whole digestate was collected and both the total solids and total suspended solids were measured. Additionally, soluble N:P:K levels were also measured.

Gas measurements for total biogas, methane, carbon dioxide and $H_2S$ were taken every 24 hours. Volatile fatty acids were measured every 24 hours from the third digester. Very low concentrations of VFA were found throughout the 35 days suggesting that conversion to biogas is rapid as substrate becomes available i.e. as the draff substrate solubilises. The pH of the third digester was also measured every 24 hours and found to lie consistently between pH 7.2 and 7.4.

Bi-carbonate alkalinity was also measured every 24 hours with a small increase noted over the period of 35 days. The digestate by the end of 35 days would typically show a bi-carbonate alkalinity of 4,500 to 5,000 mg per litre as calcium carbonate.

Again the soluble Chemical Oxygen Demand was measured every 24 hours. Reading of less than 1,000 mg per litre COD were noted. Again this would suggest that substrate is converted to biogas as soon as it becomes available.

The rate of gas production and the overall biogas and methane yield from draff benefit from a very small addition of micro-nutrients. Supplementation with very small (up to 5 ppm) quantities of cobalt, nickel and iron in the form of the chloride were seen to benefit the overall methane yield by some 10%.

After a period of 35 days of anaerobic digestion the experiment was stopped and the fertiliser N:P:K values of the digestate are measured. Potentially Toxic Elements, potential pathogens and residual methane production were also measured in the digestate. In the UK there is a code of practise with specific limits for these parameters. This is known as PAS 110—Specification for whole digestate, separated liquor and separated fibre derived from the anaerobic digestion of source segregated biodegradable materials. The draff digestate was found to meet the limits in all cases.

For draff a typical biogas yield range of 710 to 750 $m^3$ biogas per tonne draff volatile dry substance is obtained after 35 days in the digester (see FIG. 3) The methane yield after 35 days range lies between 410 and 450 $m^3$ methane per tonne volatile draff dry solids. Biogas composition is typically around 60% methane and 40% carbon dioxide.

Solubilisation of draff over the period of 35 days equates to approximately 70-80% of the original dry matter.

The rate of solubilisation and conversion to biogas when digestate high in bicarbonate alkalinity is used as the source of slurry preparation is rapid. Some 30% of the total biogas is produced within the first 48 hours. Thus, shorter slurry retention times could be optimised to take account of biogas production and solid solubilisation.

The present inventors have carried out digestion of a number of products in accordance with the present invention and the results are shown in the table below. As can be seen, a variety of starting materials have been digested in accordance with the present invention.

Anaerobic Digestion Substrates Tested - Laboratory and Plant Digesters

| No. | Substrate | Digester Retention Time | Digester Organic Dry Matter Loading | Digester Average Methane Yield |
|---|---|---|---|---|
| 1 | Malt Distillery Draff | 35 days | >5 kg's ODM/m3/day | 410 m3/tonne VSS |
| 2 | Malt Distillery Draff and Pot Ale Syrup Combined | 35 days | >5 kg's ODM/m3/day | 390 m3/tonne VSS |
| 3 | Grain Whisky Distillery Solid Co-Product (Vitagold from Girvan Distillery) | 35 days | 5 kg's ODM/m3/day | 440 m3/tonne VSS |
| 4 | Vodka Distillery Solid Co-Product - Decanter Heavy Phase Solids | 35 days | 5 kg's ODM/m3/day | 400 m3/tonne VSS |
| 5 | Canadian Whiskey Solid Co-Product - Decanter Heavy Phase Solids | 35 days | 5 kg's ODM/m3/day | 420 m3/tonne VSS |

The invention claimed is:

1. A self-sustaining method for fermentation of solid spent cereal waste products to produce a biogas and/or methane, comprising the steps of:
    (a) mixing the solid spent cereal waste products with a starter culture liquid to form a first slurry containing up to 20% of the solids by weight;
    (b) adjusting the pH of the mixture to a pH of 6.6-7.6 as necessary;
    (c) transferring the slurry to a digester and subjecting the slurry to anaerobic methogenic digestion to produce a biogas and a whole digestate;
    (d) removing whole digestate from the digester and separating the whole digestate into solid fiber and a digestate liquor;
    (e) reserving a portion of the digestate liquor;
    (f) adding the reserved portion of the digestate liquor to additional solid spent cereal waste products to form a second slurry;
    (g) transferring the second slurry to the digester without further pH adjustment; and
    (h) optionally repeating steps (d)-(g),
wherein the starter culture liquid comprises a sludge from an existing anaerobic digestion that contains a mixture of microorganisms including methanogens;
wherein the digestate liquor has high bicarbonate alkalinity buffering capacity; and
wherein the solid spent cereal waste products comprise greater than 50% solid spent cereal waste and yeast.

2. The method of claim 1, wherein the method is continuous or semi-continuous.

3. The method of claim 1, wherein the method is performed in batches.

4. The method of claim 1, wherein the solid spent cereal waste products comprise solid spent cereal waste and yeast in a ratio of 1:3 to 3:1.

5. The method of claim 1, wherein the solid spent cereal waste products comprise greater than 90% solid spent cereal waste and yeast.

6. The method of claim 1, wherein the solid spent cereal waste products comprise greater than 20% protein by dry weight.

7. The method of claim 6, wherein the solid spent cereal waste products comprise 38-44% protein by dry weight.

8. The method of claim 6, wherein the solid spent cereal waste products comprise up to 44% protein by dry weight.

9. The method of claim 1, wherein the slurry comprises a dry solids content of up to 15% of the solids by weight.

10. The method of claim 1, wherein the slurry comprises a dry solids content of up to 10% of the solids by weight.

11. The method of claim 1, wherein the starter culture liquid and the digestate liquor contains at least 3000 mg/L calcium carbonate.

12. The method of claim 1, wherein the starter culture liquid and the digestate liquor contains 4000 mg/L-5000 mg/L calcium carbonate.

13. The method of claim 1, wherein the solid spent cereal waste products comprise draff.

14. The method of claim 1, wherein the solid spent cereal waste products further comprise a material selected from the group consisting of silage, spent pot ale, pot ale syrup, and any combination thereof.

15. The method of claim 1, wherein the starter culture liquid is obtained from a waste sewage sludge treatment plant or from a conditioned microbial population obtained from the anaerobic digestion of soluble distillery waste products.

16. The method of claim 1, further comprising subjecting the slurry to milling, grinding or homogenizing prior to its transfer to the digester.

17. The method of claim 1, further comprising subjecting the slurry to acidogenic digestion prior to anaerobic methogenic digestion.

18. The method of claim 1, further comprising subjecting the non-reserved portion of digestate liquor to evaporation to produce a liquid fertilizer or a solid fertilizer.

19. The method of claim 1, further comprising aerating the anaerobic digester with a portion of the biogas.

20. The method of claim 1, wherein the reserved portion of the digestate liquor comprises 3-10% of the digestate liquor.

* * * * *